United States Patent [19]
Palmer et al.

[11] Patent Number: 4,774,959
[45] Date of Patent: Oct. 4, 1988

[54] NARROW BAND ULTRASONIC FREQUENCY ATTENTUATION BONE MEASUREMENT SYSTEM

[75] Inventors: Stuart B. Palmer, Hull; Christian M. Langton, Doncaster, both of England

[73] Assignee: Walker Sonix A/S, Worcester, Mass.

[21] Appl. No.: 818,128

[22] Filed: Jan. 10, 1986

[51] Int. Cl.[4] .............................................. A61B 10/00
[52] U.S. Cl. .................................. 128/660.06; 73/599
[58] Field of Search .................. 128/660; 73/597, 599, 73/602

[56] References Cited

PUBLICATIONS

Langton, C. M. et al, "The Measurement of Broadband UTS Attenuation in Cancellous Bone", Engrg. in Medicine, vol. 13 #2, pp. 89-91, 1984.

Bhagat, P. et al., "Microprocessor-Based System for UTS Tissue Characterization" Med. Instrumentation, vol. 14 #4, Jul.-Aug. 1980, pp. 220-223.

Ophir, J. et al., "Narrowband Pulse-Echo Technique for In-Vivo UTS Attenuation Estimation", IEEEBME Trans., vol. 32, No. 3, Mar. 1985.

Wells, P. N. T., *Biomedical Ultrasonics*, Academic Press, N.Y. 1977, pp. 110-123, 134-135.

*Primary Examiner*—Francis J. Jaworski
*Attorney, Agent, or Firm*—Henry D. Pahl, Jr.

[57] ABSTRACT

In the apparatus disclosed herein, a bone containing body member to be tested is placed between a pair of transducers and a predetermined sequence of tone signals having frequencies spanning a range from 200 to 600 kilohertz is transmitted through the body member, and the set of values representing the amplitudes of the corresponding received signals are stored. The set of values obtained with the body member between the transducer is normalized using a set of values obtained from the same sequence without the body member in place thereby to generate a third set of values which are compensated for the response characteristics of the transducer and related interfaces. A value corresponding to the rate of change of attenuation with respect to frequency is then calculated from the third set of values and is adjusted for the bone thickness, this adjusted value being related to characteristics of the body member. The bone thickness is determined by a broadband pulse echo measurement.

3 Claims, 2 Drawing Sheets

NARROW BAND ULTRASONIC FREQUENCY ATTENUATION BONE MEASUREMENT SYSTEM

BACKGROUND IN THE INVENTION

The present invention relates to apparatus measuring characteristics of a body member and more particularly to apparatus for measuring bone characteristics by means of ultrasound.

In recent years, there has been increased interest in the detection and prevention of osteoporosis and other degenerative bone conditions. In seeking methods for detecting changes in bone characteristics, it has previously been proposed to use ultrasound, particularly the measurements of the speed of transmission of acoustic waves through bone. The use of ultrasound is attractive since it is basically non-invasive and is well suited to repeated measurements or studies during medication since no ionizing radiation is employed. While substantial interesting information has been developed by these prior methods and systems, they have thus far not proven highly repeatable or reliable in diagnosis or in the large scale screening of actual populations.

Among the several objects of the present invention, may be noted the provision of a novel apparatus for measuring characteristics of bones in vivo using ultrasound; the provision of apparatus for measuring bone characteristics by ultrasound which is highly reliable and repeatable; the provision of such apparatus which provides measurements which are well correlated with changes in bone conditions such as those occurring with the onset of osteoporosis. The provision of such apparatus which is suitable for screening large populations; the provision of such apparatus which is easily operated and which is of relatively simple and inexpensive construction; other objects and features will be in part apparent and in part pointed out hereinafter.

SUMMARY OF THE INVENTION

Briefly, apparatus according to the present invention is suited for measuring characteristics of a body member and employs a transmitting transducer adapted to be placed on one side of the body member and a receiving transducer adapted to be placed on the opposite side of the body member. An oscillator is employed for generating a tone signal of preselectable frequency of a predetermined time interval and the oscillator is controlled to generate a predetermined sequence of tones signals having frequencies spanning a range from 200 to 600 kilohertz.

The apparatus is operated to generate a first sequence without the body member being between the transducers and to store a first set of values representing the amplitudes of the corresponding signals received by the receiving transducer. A second sequence is then generated with the body member being in place between the transducers and a second set of values is stored which represent the amplitudes of the corresponding signals received by the receiving transducer. The second set of values is adjusted based on the first set of values thereby to generate a third set of values which are compensated for the response characteristics of the transducers and related interfaces and thus better represent attenuation at each frequency. From the third set of values a value corresponding to the rate of change of attenuation with respect to frequency is calculated. This value has been found to be well correlated with the changes in body characteristics.

BRIEF DESCRIPTION OF THE DRAWINGS

Corresponding reference characters represent corresponding parts throughout the several views of the drawings.

DESCRIPTION OF THE PREFERRED EMBODIMENT

Figure 1:
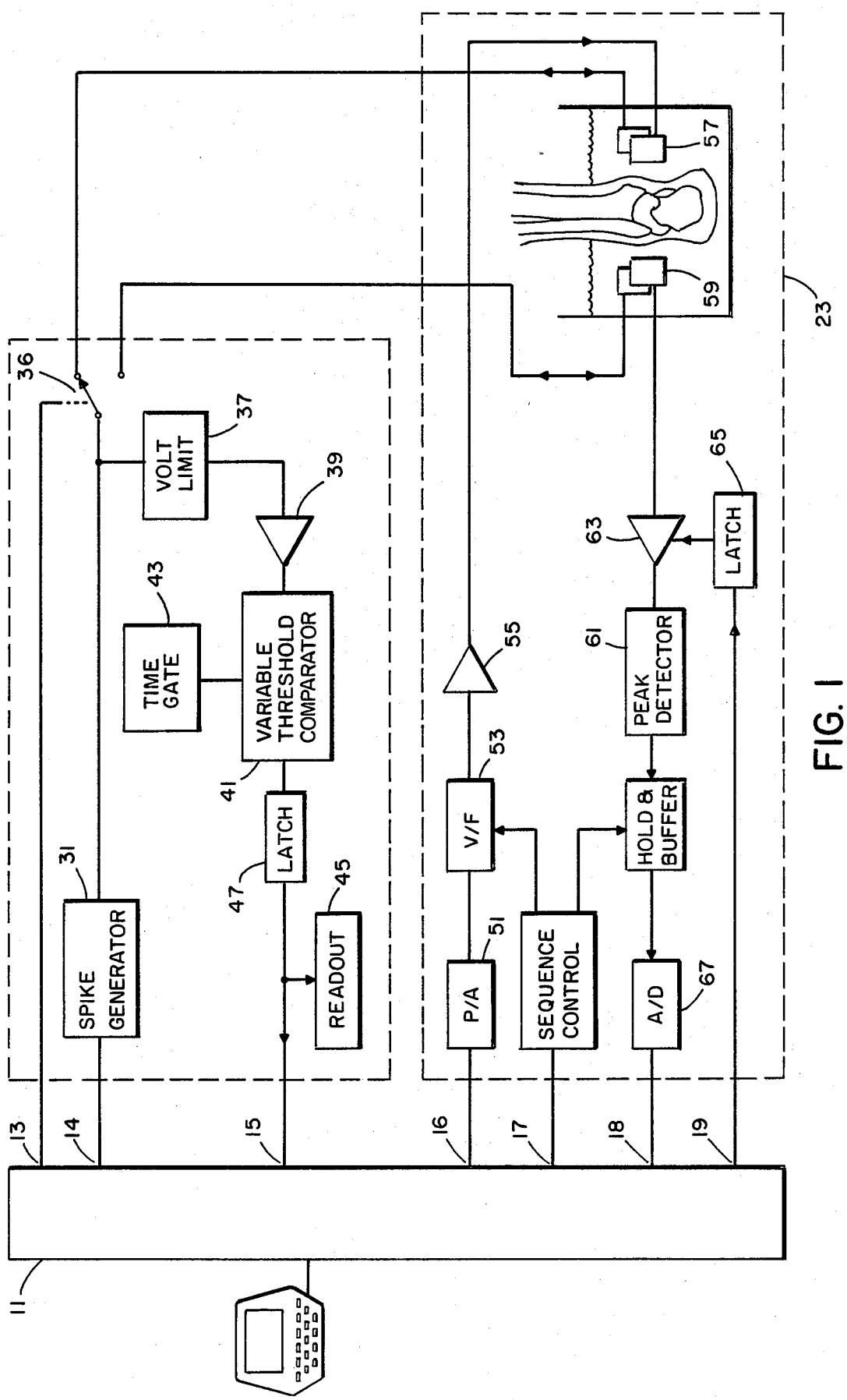
FIG. 1 is a schematic block diagram of an ultrasonic body member measurement apparatus constructed in accordance with the present invention.

As is increasingly the case with investigative instruments in general, the sequence of operations of the various elements of the system of the present invention are controlled by a general purpose programmable computer. In addition, raw measurement values obtained by the special purpose elements of the system are normalized and further or resultant values are calculated by the computer. With reference to FIG. 1, such a general purpose computer is indicated by reference character 11. As is conventional, the computer 11 will typically include a keyboard for operator input, CRT display for providing information to the operator of the system, and a disk drive for storing both intermediate and the final results.

The computer 11 is provided with several digital ports, designated by reference characters 13-19 which permit the computer to communicate the special purpose hardware elements employed in the system of the present invention. In general, the special purpose hardware components may be divided into two groupings, the bone width measurement system elements, designated generally by reference character 21, and the attenuation measurement system elements, designated generally by reference character 23.

In the embodiment illustrated, the bone width measurement system 21 and the attenuation measurement system 23 each employ a pair of ultrasonic transducers, one adapted to be located on each side of the body member whose characteristics are to be measured. In initial implementations of the system of the present invention, the use of two sets of transducers has thus far been found preferable since the characteristics desired for the two different measurements have likewise differed. However, it should be understood that by specially constructing a transducer for this particular end use application, it should be feasible to provide both functions in one pair of transducers, i.e. using suitable switching between the various circuit elements.

As is known in the prior art, the heel bone (os calcius) is a convenient site for measuring representative bone characteristics. It is a relatively large bone section yet is relatively accessible, the flesh on either side being relatively thin. In order to effectively couple acoustic energy, it is desirable that the heel bone be immersed in a water bath with the transducers. As indicated previously, the particular embodiment described herein employs two pairs of transducers, each pair comprising one transducer on each side of the body member. The body member, i.e. the heel bone, is preferably held between the pair of transducers in a suitable jig or clamp (not shown). To permit the heel to be moved from between one pair of transducers to a location between the other pair of transducers, it is convenient to provide a jig or clamp which allows movement fore and aft, i.e. in a plane perpendicular to the axis between each pair of transducers. It has been found that the best acoustic coupling is obtained if a mild wetting agent is added to improve wetting and removal of bubbles. While immersion is presently preferred as a method of coupling the transducers, it should be understood that other expedients such as compliant pads and coupling gels might also be used.

The bone width measurement system 21 is per se of quite conventional construction, and can, in fact, be easily implemented by interfacing a commercially available echo-ranging system with the computer 11. A broad-band spike generator 31 is triggered by the computer to initiate a ultrasonic ranging operation, the output of the spike generator 31 being applied to one or the other of the transducers 33 and 35. Selection of the particular transducer is made by means of an electronic switch 36. The selected transducer is also connected, through a voltage limiter 37 and a suitable preamplifier 39 to a variable threshold comparator 41. Comparator 41 is controlled by a manually adjustable time gate circuit 43 so that, of the various echos which may come back, only ones falling within a preselected distance range are considered. This allows the operator to select the tissue/bone interface (which is of interest) as opposed to the water/tissue interface. The distance measurement corresponding to the time between triggering and the selected echo is latched at 47 and presented on a readout 45, so that the operator can verify that the value obtained corresponds to observed physical position. The distance measurement is present on latch 47 can be read by the computer 11.

As is described in greater detail hereinafter, the bone width measurement circuitry 21 is operated to provide a pair of measurements each indicative of the distance from the respective transducer to the bone. The computer 11 then calculates the bone thickness from these measurements and the known distance between the transducers. As indicated previously, the echo ranging system itself is essentially conventional. A particularly adaptable form of such a system is the Echoscan 1502 manufactured by PAR Scientific Instruments of Denmark.

Referring now to the attenuation measurement section of the circuitry, an interrogating tone burst is generated when the computer 11 loads a digital value corresponding to the desired frequency into a digital-to-analog converter 51. The voltage level obtained provided by the converter 51 is applied to a voltage-to-frequency converter 53 which actually provides the desired narrow band tone. This tone signal is then applied, through a suitable driving amplifier 55, to a transmitting transducer 57.

On the opposite side of the body member being tested is a receiving transducer 59. Signals picked up by the receiving transducer 59 are applied, through a gain controlled amplifier 63, to a radio frequency-to-DC converter and peak detector 61 (essentially a linear rectifier circuit). The gain of amplifier 63 is controlled by a digital value which is loaded into a latch 65 from the computer port 19. The output signal from the amplifier 63 is in turn applied to an analog-to-digital converter 67 which provides a digital value which can be read by the computer 11 through port 18.

Figure 2:
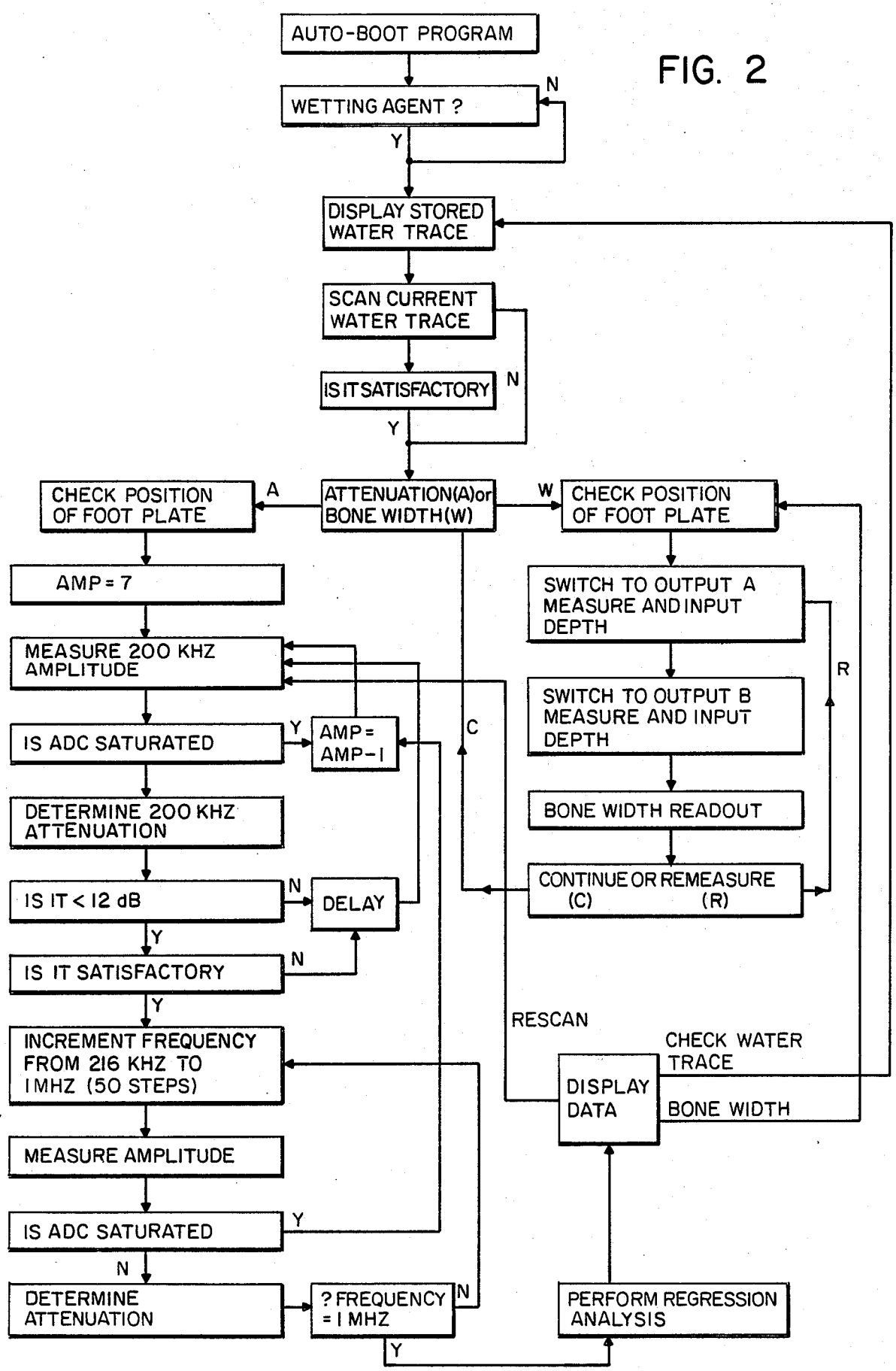
FIG. 2 is a flow chart of a computer program employed in the apparatus of FIG. 1.

With reference to the flow chart of FIG. 2, the overall operation of the system of FIG. 1 is as follows. After the operating system is booted into the computer, the operator of the system is interrogated, i.e. through the CRT display, as to whether wetting agent has been added. The operator provides his answers through the keyboard. Once the operator's answers are satisfactory, the program moves on an displays a currently stored plot or trace of the water path, i.e. a plot of the transfer characteristic between the two transducers 57, 59 with no body member present, and initiates a current attenuation measurement, again without the patient's heel member being between the transducers. The current trace is also displayed allowing the operator to determine if any exceptional changes have occurred such as would indicate a failure in some component. As is described hereinafter, the newly obtained data is stored and used in adjusting the attenuation measurements taken with the patient's heel in position between the transducers so as to compensate for the response characteristics of the transducers and related interfaces.

Assuming that satisfactory current water trace data is obtained, either from the stored data or by fresh measurement, the operator is then allowed to select whether a bone width or an attenuation measurement is to be taken. Assuming that bone width measurement is selected first, the operator is asked to check that the foot clamp or jig is positioned between the appropriate pair of transducers. Once the operator verifies that this is the case, the computer switches to the A transducer and measures distance from the transducer to the heel bone as described previously. The system then switches to transducer B and measures and stores the distance from that transducer to the bone. The computer then calculates the bone width by subtracting the two obtained measurements from the known distance between the two transducers and stores this value for use in normalizing the calculations described hereinafter.

Once the bone width measurement has been obtained, the program returns to the selection stage where the operator can select to perform the attenuation measurement instead of the bone width measurement. Again, the program prompts the operator to check the position of the foot holding jig or clamp to assure that the patient's heel bone is located between the appropriate pair of transducers. Once the operator has provided the proper affirmation, an initial value is loaded into the latch 65 which controls the gain of amplifier 63. For the purpose of description, a sequence of selectable gain values are simply designated as 7 through 1, in order of decreasing gain. The initially selected value is assumed to be 7.

Once the initial gain value is set, the computer then triggers the generation of a single burst at the lowest frequency used, e.g. 200 kilohertz, and reads the corresponding value picked up by the receiving transducer 59, i.e. by reading the output from the analog to digital converter 67. The initial measurement is checked to determine if the analog to digital converter 67 is saturated. If the converter is saturated, the gain level is decremented, and the test is repeated. The test is repeated until the analog-to-digital converter 67 is not saturated.

Once a non-saturated value is obtained from the analog to digital converter 67, an attenuation value corresponding to the 200 kilohertz signal frequency is calculated, and this value is checked to make sure it is within an acceptable range. If it is not, the operator is prompted to investigate and take remedial action, e.g. making sure the patient's foot is properly positioned and that the surfaces of the foot and transducer are not coated with bubbles and so forth.

Once the base (200 kilohertz) attenuation value is determined to be satisfactory, the program operates to generate a sequence of narrow band tone signals having frequencies spanning a range from 200 to at least 600 kilohertz. In practice it has been found useful to span a range from 200 kilohertz to 1 megahertz, though only the range from 200 kilohertz to 600 kilohertz is used for the slope value computations described hereinafter. While the apparatus described herein steps through frequency increments in a regular progression from low to high, it should be understood that the different frequencies could be generated in any order and that the number of frequencies required is only that necessary to define with acceptable accuracy the slope value whose calculation is described hereinafter. Similarly, a swept frequency generator might also be used, though the use of discrete frequencies is presently deemed preferable and is more amenable to computer control and analysis.

For each tone, the received amplitude is measured and stored. Throughout the measurement, the computer checks to make sure the analog-to-digital converter 67 is not saturated. As each amplitude measurement is obtained, it is stored and a corresponding attenuation value (T1) is calculated and stored. The attenuation value is calculated according to the formula $$T1 = 20 \log (A2/A1)$$

where A2 is the amplitude measured with the heel in place and A1 is the amplitude measurement through water alone. The sequence terminates when the last frequency in the predetermined sequence is reached, e.g. 1 megahertz in the embodiment illustrated. After satisfactory data is obtained for the entire sequence of frequencies, each attenuation value obtained with the body member in place value is normalized using the corresponding value from the set of values obtained without a body member between the transducer. This calculation procedure thus results in an adjusted set of values T1 which are, in effect, compensated for the response characteristics of the transducers and related interfaces, both physical and electrical.

From the compensated set of values, the computer calculates a value (S1) corresponding to the rate of change of attenuation with respect to frequency. In addition, the computer calculates a normalized slope value S2 based upon the bone width measurement. The normalized slope is calculated according to the formula $$S2 = S1(W0/W1)$$

where W1 is the actual bone width measurement and W0 is a constant corresponding to a nominal or typical value for width. This value is displayed and stored as indicated previously. This normalized slope value S2 has been found to correlate very reliably with changes in bone characteristics which occur with the onset of osteoporosis, and is thus believed to be highly useful as a mechanism or indicator for screening large populations or for monitoring progress during medication or other treatment.

In view of the foregoing, it may be seen that several objects of the present invention are achieved and other advantageous results have been attained.

As various changes could be made in the above constructions without departing from the scope of the invention, it should be understood that all matter contained in the above description or shown in the accompanying drawings shall be interpreted as illustrative and not in a limiting sense.

What is claimed is:

1. Apparatus for measuring characteristics of a bone containing body member, said apparatus comprising:
    a transmitting transducer adapted to be placed on one side of said body member;
    oscillator means for generating a tone signal of preselectable frequency for a preselected time interval;
    means for controlling said oscillator means to generate a predetermined sequence of tone signals having frequencies spanning a range from 200 to 600 kilohertz;
    amplifier means for applying said tone signals to said transmitting transducer;
    a receiving transducer adapted to be placed on the opposite side of said body member, and to receive signals emitted by said transmitting transducer through said bone containing body member;
    means for operating said controlling means to
    (A) generate a first said sequence without said body member being between said transducers and to store a first set of values representing the amplitudes of the corresponding signals received by said receiving transducer,
    (B) and to generate a second said sequence with said body member between said transducers and to store a second set of values representing the amplitudes of the corresponding signals received by said receiving transducer;
    means utilizing said second set of values and said first set of values for generating a third set of values generally in accordance with the formula $$T1 = 20 \log (A2/A1)$$

where A2 is a respective second value and A1 is a respective first value;
    means utilizing said third set of values and the corresponding tone frequences for calculating and reading out a value corresponding to the rate of change of attenuation of the body member with respect to tone frequency.

2. Apparatus for measuring characteristics of a bone containing body member, said apparatus comprising:
    a transmitting transducer adapted to be placed on one side of said body member;
    oscillator means for generating a tone signal of preselectable frequency for a preselected time interval;
    means for controlling said oscillator means to generate a predetermined sequence of tone signals having frequencies spanning a range from 200 to 600 kilohertz;
    amplifier means for applying said tone signals to said transmitting transducer;
    a receiving transducer adapted to be placed on the opposite side of said body member, and to receive signals emitted by said transmitting transducer through said bone containing body member;
    means for operating said controlling means to
    (A) generate a first said sequence without said body member being between said transducers and to store a first set of values representing the amplitudes of the corresponding signals received by said receiving transducer, (B) and to generate a second said sequence with said body member between said transducers and to store a second set of values representing the amplitudes of the corresponding signals received by said receiving transducer;

means utilizing said second set of values and said first set of values thereby to generate a third set of values which are calculated generally in accordance with the formula $$T1 = 20 \log (A2/A1)$$

where A2 is a respective second value and A1 is a respective first value;

means utilizing said third set of values and the corresponding tone frequencies for calculating and reading out a value (S1) corresponding to the rate of change of attenuation of the body member with respect to tone frequency;

means responsive to said controlling means for generating a broad-band pulse;

amplifier means adapted to be selectively connected to a selected one of a pair of transducers for applying said broad-band pulse to said selected transducer, one transducer being on each side of said body member;

means adapted to be selectively connected to a selected one of a pair of transducers for receiving echos reflected back to said selected transducer from interfaces within said body member and for timing the transit time from the transmitted pulse, said controlling means being operative to obtain transit time from both of the pair of the transducers;

means for determining, from the transit times so obtained, a value (W1) representing the thickness of bone present in said body member; and means for calculating and reading out a value (S2) determined essentially by the formula $$S2 = S1(W0/W1)$$

where W0 is a constant.

3. Apparatus as set forth in claim 2 wherein said pair of transducers is in addition to the aforesaid transmitting transducer and receiving transducer.

* * * * *